United States Patent [19]
Hughes

[11] Patent Number: 4,690,332
[45] Date of Patent: Sep. 1, 1987

[54] SINGLE INLET PREPACKAGED INHALER

[76] Inventor: Nathaniel Hughes, 1934 Sonora Rd., Palm Springs, Calif. 92662

[21] Appl. No.: 652,754

[22] Filed: Sep. 18, 1984

Related U.S. Application Data

[63] Continuation-in-part of Ser. No. 555,703, Nov. 28, 1983, Pat. No. 4,635,857.

[51] Int. Cl.[4] .............................................. A61M 11/06
[52] U.S. Cl. ............................... 239/338; 128/200.18; 128/200.21; 239/590.3; 239/590.5; 261/78.2; 261/DIG. 65
[58] Field of Search ............... 239/102, 338, 370, 590, 239/590.3, 590.5, DIG. 20, DIG. 23, 102.1; 128/200.18, 200.21; 261/78 A, DIG. 65, 78.2

[56] References Cited

U.S. PATENT DOCUMENTS

| | | |
|---|---|---|
| 3,230,924 | 1/1966 | Hughes . |
| 3,652,015 | 3/1972 | Beall ..................................... 239/338 |
| 4,116,387 | 9/1978 | Kremer, Jr. et al. ................ 239/338 |
| 4,228,795 | 10/1980 | Babington ........................... 239/338 |
| 4,241,877 | 12/1980 | Hughes ............................. 239/590.3 |
| 4,301,970 | 11/1981 | Craighero ........................... 239/338 |

OTHER PUBLICATIONS

"Aerosolized Drug Delivery Accessories" by A. J. Curie, S. Ertefaie & J. J. Sciarra, Aerosol Age, Mar. 1984, pp. 24–26.

"Metered–Dose Aerosol Administration" by Martin Tobin, MD, (paper presented at American Assn. of Respiratory Therapy 28th Annual Convention and Exposition, Oct. 30–Nov. 2, 1982, New Orleans, LA), pp. 16–20.

Primary Examiner—Andres Kashnikow
Assistant Examiner—Michael J. Forman

[57] ABSTRACT

An apparatus (22) for applying medication as an aerosol includes a fluid supply channel (96) for supplying fluid from a container (24) of a mixture of propellant and medication wherein the fluid supply channel is adapted to accept a nozzle (26) coupled to the container for receiving the mixture and wherein the fluid supply channel has a first cross-sectional area. A first chamber (30) at a first downstream portion from the fluid supply channel has a second cross-sectional area (34) for expanding the fluid and for forming a first flow condition. A chamber (36) is supplied downstream from the fluid supply channel for changing the first flow condition.

1 Claim, 12 Drawing Figures

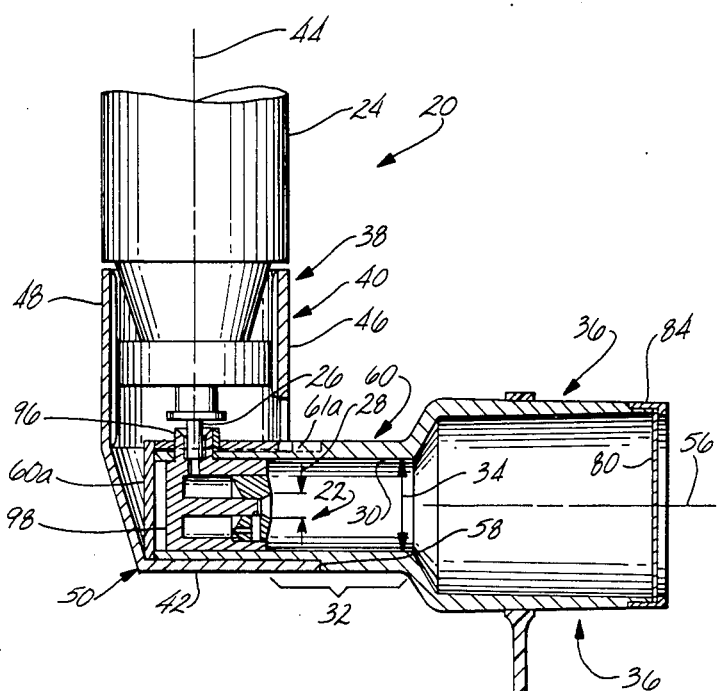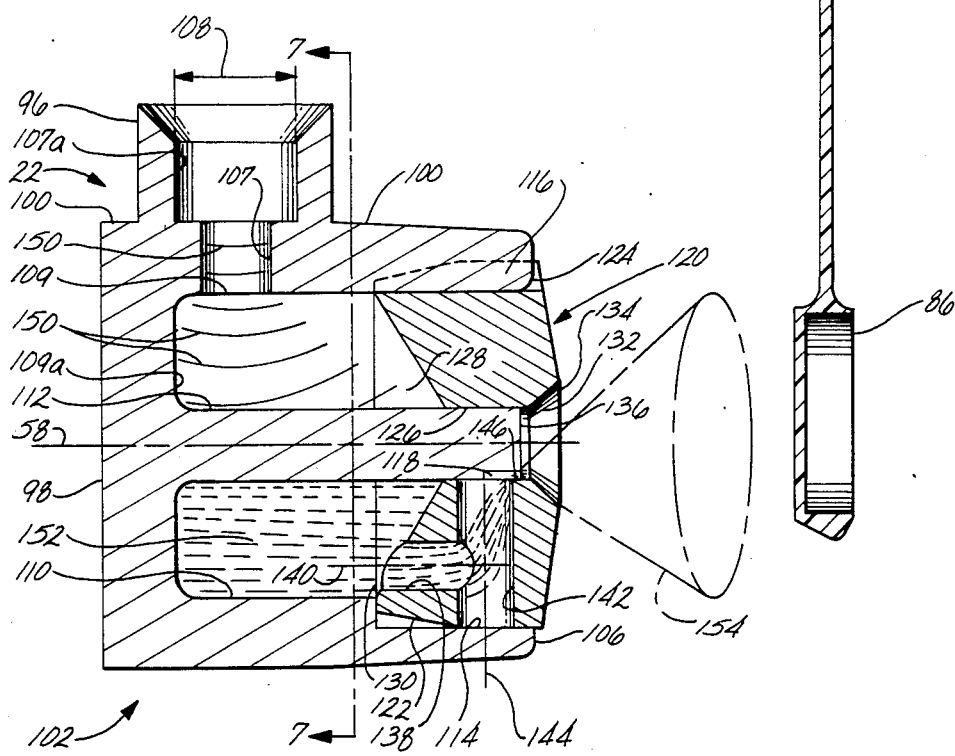

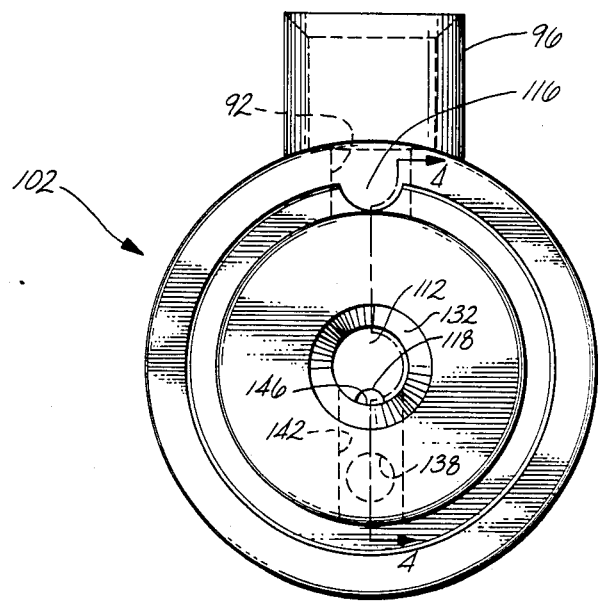
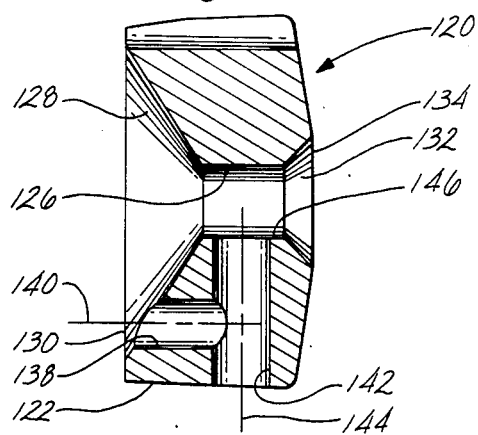
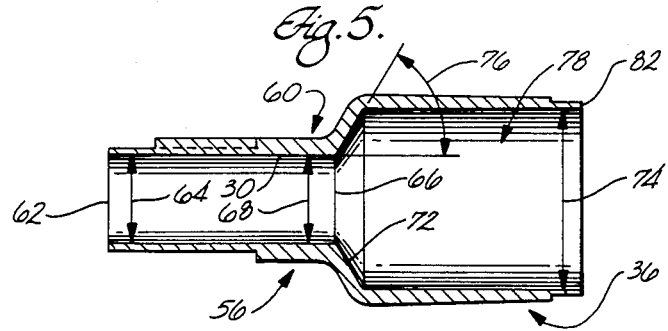

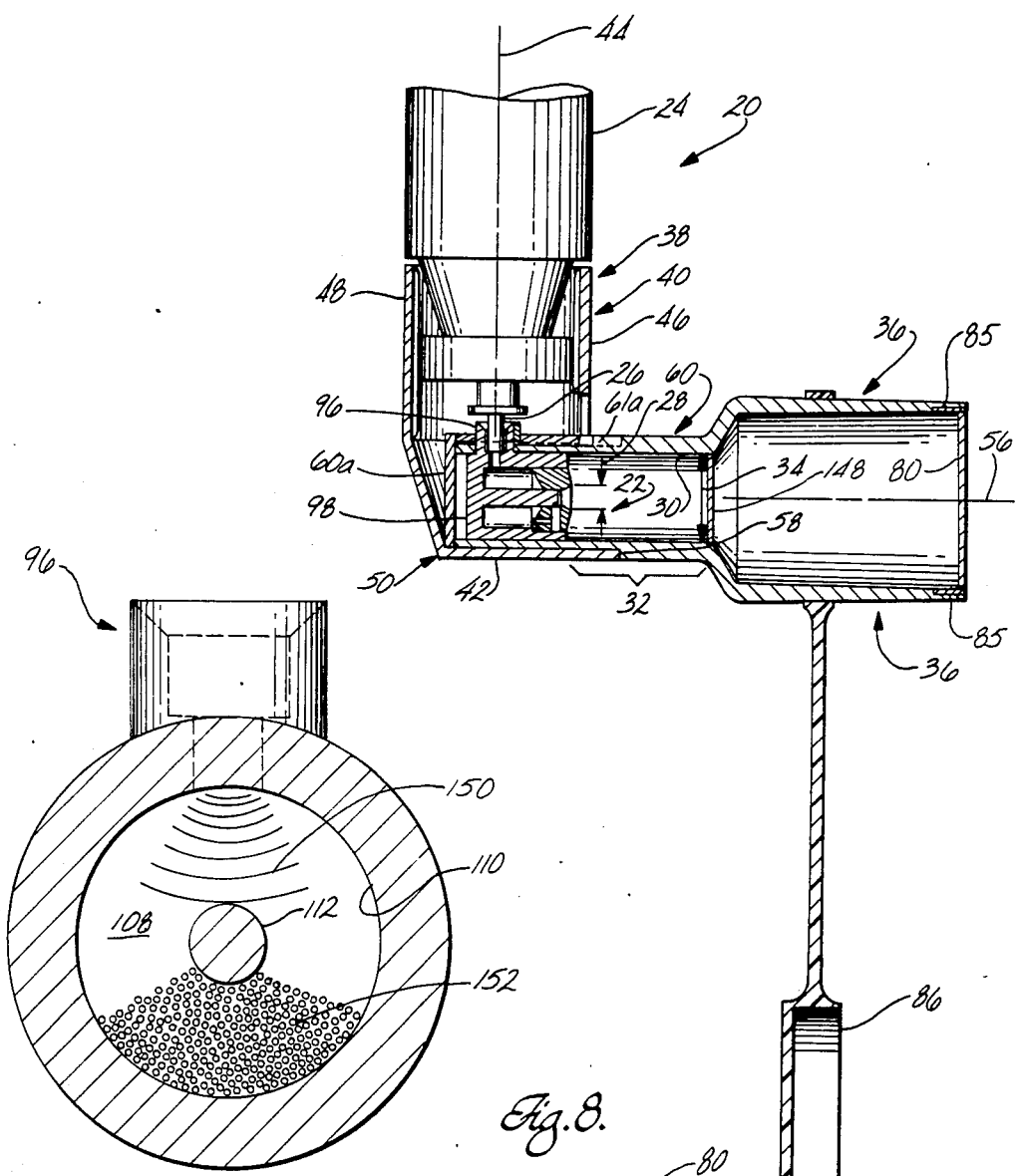

SINGLE INLET PREPACKAGED INHALER

CROSS-REFERENCE TO RELATED APPLICATIONS

This application is copending with a related application entitled "Aerosol Producing Device", Ser. No. 652,740, filed Sept. 18, 1984 and is a continuation-in-part of an an application entitled "Atomizing Apparatus", Ser. No. 555,703, filed Nov. 28, 1983, now U.S. Pat. No. 4,635,857, issued Jan. 13, 1987.

TECHNICAL FIELD

This invention relates to medicant applicators and more specifically to metered dose inhalers.

BACKGROUND ART

Medicated aerosol dispensers are generally well known in the art, such as anti-asthmatic medication dispensers providing medication from a propellant-charged canister through a device for creating aerosol including a mouth piece. These devices generally created an aerosol having a spray with oversized liquid particles with a significant forward velocity which impacted the patient's mouth or lips when the inhaler was operated. There is no compact device which could deliver an aerosol from such a canister having droplets of one to three microns monodispersed size. A 10-centimeter (4-inch) spacer was typically attached to the inhaler in an attempt to provide uniform particle size, which did not succeed. These spacers produced a noncompace cumbersome inhaler with most of the medicine trapped in the device and not delivered to the patient.

Prior inhalers also produced an aerosol having a cold temperature which was uncomfortable to the patient. Sudden expansion of the liquified propellant/liquid medication mixture upon ejection from the canister resulted in severe cooling of the spray, and severe inertial impaction on the patient's nose and/or throat.

U.S. Pat. No. 4,241,877 to Hughes shows a vortex generating device in FIGS. 5A, 5B, and 6, wherein a gas and a liquid pass into a flow passage together from an inlet. The mixture flows about a rod and forms vortices thereabout and enters a bore along a portion of the rod after which the mixture exits the device through a constricted bore to a semispherical diverging outlet. The liquid is partially atomized as it leaves the bore in the inlet and becomes fully atomized as it leaves the semispherical diverging outlet in a vortical gas stream. A device is also shown where a gas and liquid under pressure are supplied together through an inlet member to a transversely extending rod for formation of vortices. The vortices flow in a direction coaxial with the rod to a constricted outlet bore and to a semispherical diverging outlet. The vortices also flow along auxiliary passages toward the constricted bore portion to combine with the previously-mentioned coaxial flowing vortices.

The Hughes '877 device is suitable for relatively high mass flow rates, but would not be suitable for use with the propellant-charged canisters containing a relatively low propellant-to-medication liquid ratio. With such canisters, it is desirable to minimize the proportion of propellant in each dose and maximize the vortical action of the mixture while flowing through the transducer. Furthermore, it would be difficult and expensive to manufacture a device as indicated in the Hughes '877 patent and still provide the aerosol production capabilities required in conjunction with the propellant-charged canister.

Previous devices also suffered from oropharyngeal drug deposition due to the size and velocity of the aerosol particles. A paper by Martin Tobin, M.D., presented at American Association for Respiratory Therapy, 28th Annual Convention and Exposition, Oct. 30–Nov. 2, 1982, New Orleans, La., describes the various attempts to minimize the oropharyngeal deposition. One device incorporated a cylindrical tube, resulting in a reduction in oropharyngeal deposition. A pear-shaped tube, the design of which was chosen to simulate the shape of an aerosol cloud as it leaves the metered-dose inhaler, did not produce any additional reduction in oropharyngeal drug deposition.

U.S. Pat. Nos. 3,230,924 and 4,190,203 discuss the use of a resonator in conjunction with gas flow. The resonator disclosed in U.S. Pat. No. 4,190,203 assists in atomizing the aerosol produced from the transducer, but is cumbersome.

The present invention overcomes these deficiencies in the prior devices. The present device provides an aerosol delivered at a very small or negligible velocity thereby minimizing the impact of the aerosol on the patient. The device provides a mist having droplets which are uniform in size regardless of the variation in range of pressure provided through the liquified propellant in the canister or the amount of medicament atomized.

A chamber approximately one-fourth the size of the spacer of the prior devices can be used in the present device in order to create the low or zero velocity aerosol. Additionally, the warm temperature of the aerosol is more suitable to the body temperature of the patient for inhalation. The droplets produced by this device are always one to three microns monodispersed as necessary for full and complete penetration of the bronchial tree and the coating of the receptor sites. There is negligible or no deposition in the device itself as diametrically opposed to the prior devices. The performance of prior devices is shown in a paper entitled "Aerosolized Drug Delivery Accessories" by Cutie, et al. in "Aerosol Age", March 1984, which indicates that only 10–15% of the dose "actuated into the respiratory airways" as opposed to over 90% with the present invention.

DISCLOSURE OF THE INVENTION

An apparatus and method are disclosed for applying medication as an aerosol. Means are provided in the apparatus for supplying an aerosol from a container of a mixture of propellant and medication, wherein the aerosol supplying means is adapted to accept a nozzle coupled to the container for receiving the mixture and wherein the aerosol supplying means has a first cross-sectional area. A first expansion chamber is provided at a first downstream portion from the aerosol supplying means having a second cross-sectional area for expanding the aerosol and for forming a first flow condition. Means downstream from the aerosol supplying means is provided for changing the first flow condition.

BRIEF DESCRIPTION OF THE DRAWINGS

FIG. 1 is a side-sectional view of an embodiment of a metered-dose inhaler having a single-inlet transducer assembly for creating an aerosol and an expansion chamber and screen for further modifying the aerosol;

FIG. 2 is a schematic and side-sectional view of the transducer assembly of the device of FIG. 1;

FIG. 3 is a front elevation view of the transducer assembly of FIG. 2;

FIG. 4 is a side section of a lens element for use in the transducer assembly of FIG. 3 taken along lines 4—4 of FIG. 3;

FIG. 5 is a side-sectional view of a portion of the device of FIG. 1 showing two expansion chambers;

FIG. 6 shows an alternative embodiment of the device of FIG. 1 with an additional screen;

FIG. 7 shows a schematic of a transverse cross section of the transducer assembly of FIG. 2 showing shockwaves and vortices, FIG. 8 shows a resonant screen for use in the inhaler of FIG. 1;

MODES FOR CARRYING OUT THE INVENTION

Figure 9:
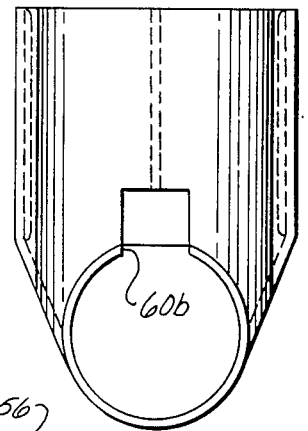
FIG. 9 shows a front elevation view of a body portion of the inhaler.

It will be understood that the description herein of the apparatus and its use includes a description of the method for applying medication as an aerosol.

In FIG. 1, an apparatus for applying medication as an aerosol in the form of inhaler 20 is shown. The inhaler includes means for supplying an aerosol in the form of a transducer assembly 22 from a container 24 of a mixture of propellant and medication (not shown) wherein the transducer assembly is adapted to accept a nozzle 26 coupled to the container 24 for receiving the mixture and wherein the transducer assembly has a first cross sectional area indicated at 28. A first expansion chamber 30 is provided at a first downstream portion indicated at 32 from the transducer assembly having a second cross sectional area indicated at 34 for expanding the aerosol (not shown) and for forming a first flow condition. Means is provided (shown generally at 36) downstream from the transducer assembly 22 for changing the first flow condition.

Considering the inhaler 20 in more detail with respect to FIG. 1, the inhaler 20 includes a first body portion 38 for accepting and retaining the container 24 and for partially enclosing the transducer assembly 22. The container 24 has a structure and function similar to metered dose containers generally known in the art. The first body portion 38 is generally shaped in the form of an elbow having a hollow, cylindrical, generally upwardly extending vertical arm 40 and a hollow, cylindrical, generally forwardly extending (with respect to the remainder of the inhaler 20) horizontal arm 42. (The directional terms used herein, such as horizontal, vertical and upward are intended to be used for reference to the drawings only and are not to be construed as a limitation on the structure or function of the device.) The vertical arm 40 extends along a verticle axis 44. The front half 46 of the verticle arm 40 extends vertically substantially all the way to the horizontal arm 42, except for a slot, rectangular in frontal view, for allowing insertion of the transducer (described below). The rear half 48 of the vertical arm 40 extends vertically downward to a bend 50 forming the back half and the bottom portion of horizontal arm 42.

Horizontal arm 42 extends from the bend 50 substantially horizontally, as shown in FIG. 1, about a horizontal axis 56. The vertical axis 44 is normal to a plane containing the horizontal axis 56. The horizontal arm 42 is substantially right circular cylindrical in vertical transverse cross section, as shown in FIG. 9. The horizontal arm 42 extends forward about and past the transducer assembly 22 (in assembled form) to the end 58 of the first body portion 38. The outer surface of the horizontal arm 42 terminates flush with the outer surface of second body portion 60.

The interior surface of horizontal arm 42 is also substantially right circular cylindrical in vertical transverse cross section and includes an end plate 60a at the left end, as seen in FIG. 1, of the horizontal arm 42. A key-way 60b (FIG. 9) is cut in the top surface of the cylindrical portion of horizontal arm 42 for guiding and retaining the inlet of the transducer assembly, to be described more fully below, as the assembly is placed in the horizontal arm.

The first body portion 38 is formed generally such that it is compact and partly provides protection to the transducer assembly 22 and to the container 24. The external dimensions of the first body portion 38, along with second body portion 60 are such that the inhaler 20 is compact and easily fits in the hand and may fit into a pocket. The first body portion 38 along with the second body portion 60 are preferably made of polypropylene but may be made of other medical grade organic polymers providing structural support and desirable surface qualities after molding.

The second body portion 60 is for retaining and positioning the transducer assembly 22 and for changing the flow conditions of the aerosol subsequent to aerosol production in the transducer assembly. The latter function depends on the interior design of the second body portion 60.

The second body portion 60 has a rear portion whose outside and inside diameters are approximately one-half the outside and inside diameters, respectively, of the immediately adjacent forward portion. The rear portion extends within and mates with the interior surface of horizontal arm 42. The upper surface has a horizontally extending "U"-shaped cut (as viewed from above) made from the edge of a rear portion therein for accommodating the vertical inlet (to be described below) of the transducer assembly 22. The remainder of the rear portion is substantially cylindrical in vertical transverse cross section and extends from the rear portion of transducer assembly 22 to the remainder of second body portion 60. Midway along the outer surface of the second body portion is a perimetrical flanged surface 61 for mating with the end 58 of the horizontal arm. At the top, as viewed in FIG. 1, a rectangular key 61a extends generally horizontally rearward from the flanged surface 61 to mate with the key-way 60b (FIG. 9) in the top of the horizontal arm.

As shown in FIG. 5, the second body portion extends from the rear end 62 having a preferred inside diameter indicated generally at 64 of approximately 0.467 inch to the end 66 of the first expansion chamber wherein the inside diameter, indicated generally at 68 is preferably 0.480 inch. At the end of the first expansion chamber 30 in the first downstream portion 32 the inside dimensions of the second body portion 60 increase to form a diverging conical portion 72 wherein the inside diameter 74 of the second body portion is increased to preferably 0.940 inch. The angle 76 of the diverging conical portion 72, from the horizontal is approximately 60°. The diverging conical portion 72 and the remainder of the second body portion 60 form a second expansion chamber 78. The outside dimensions of the second body portion 60 are generally designed for structural integrity and compactness secondarily to the inside dimensions discussed above. The inside length of the first expansion chamber 32 is preferably 1.230 inch, and the inside length of the second expansion chamber from the end of the first is 1.273 inch.

As shown in FIG. 1, the first and second body portions 38 and 60, respectively, are joined to form the exterior housing defining the inhaler 20. The key 61a coupling the first and second body portions at the top of the horizontal arm 42 generally prevents rotation of the first body portion with respect to the second body portion. The mutually adjacent surfaces of the first and second body portions may be bonded by ultrasonic or sonic welding to provide an airtight seal for preventing entrainment of air and preventing rotation of the two portions with respect to each other.

As shown in FIG. 1, a vapor screen net or resonant screen 80 (FIG. 8) or square grid is positioned adjacent the outside horizontal rim 82 of the second body portion 60 forming the second expansion chamber 78. The resonant screen 80 is retained in place against the rim 82 by a screenretaining rim cap 84. The rim cap 84 is preferably ultrasonically welded to the second body portion 60 to prevent removal of the cap and resonant screen 80. The screen is preferably formed of a nylon lattice having an extreme diameter of 0.980 inch and a square lattice opening dimension of 0.060 inch×0.060 inch. Each lattice member is preferably 0.012 inch across the face and 0.024 inch deep from one face of the screen to the other. The outside diameter of the horizontal rim or lip of the second body portion is also preferably 1.020 inch for retaining the resonant screen in conjunction with the rim cap 84.

Alternatively, as shown in FIG. 6, the resonant screen 80 may have a diameter of 0.910 inch and bonded to a frame 85 having an outside diameter of 1.010 inch. The bonded screen is then placed on the inside of the second expansion chamber and bonded thereto. The resonant screen and frame are positioned in the end of the second expansion chamber such that the outside surface of the resonant screen is flush with the rim of the second expansion chamber.

A cap 86 may be provided anchored around part of the second body portion 60 for capping the end of the inhaler at the second body portion 60 for protecting the resonant screen 80 and for preventing entry of foreign matter. The cap 86 may be made of nylon.

The outside dimensions of transducer assembly 22 are chosen so that the assembly is retained in and held by the interior walls of the second body portion 60 at the rear portion thereof. The joinder of the two is preferably a snap-in or snug fit. The inlet 96 of transducer assembly 22 is placed in the "U"-shaped key in the rear portion of second body portion 60. The remainder of the rear portion of second body portion 60 substantially surrounds the sidewalls of transducer assembly 22. The back edge 98 of the transducer assembly 22 is positioned adjacent the end plate 60a of the horizontal arm. The transducer assembly 22 is held by the key portion of second body portion 60 and is substantially surrounded by second body portion 60.

Considering the transducer assembly 22 in more detail with respect to FIGS. 2–4, FIG. 2 shows the transducer assembly 22 separate from the remainder of the inhaler. The transducer assembly 22 is substantially right circular cylindrical in external dimension and comprises a vertically oriented inlet 96 previously mentioned. The inlet 96 is a single fluid inlet oriented about the vertical axis 44 for accepting the nozzle 26, the medicated mixture from the nozzle 26 after actuation and for introducing the fluid to the remainder of the transducer assembly 22. The rear surface of the inlet 96 extends vertically downward to the upper surface 100 of the transducer body 102. The flat rear surface 98 is substantially circular and closes the rear portion of the transducer body 102.

The front portion of the inlet 96 extends vertically downward to the upper surface 100 of the transducer body 102. The transducer body 102 extends along the horizontal axis 58. The exterior portion of the transducer body 102 terminates at a forward circumferential rim 106. The outside dimensions of the transducer body 102 are formed so as to provide an airtight fit with the inside surfaces of the second body portion 60 which will enclose the transducer body. This prevents rotation of the transducer assembly with respect to the second body portion 60 and prevents entrainment of air during operation of the inhaler. The transducer assembly, including the lens portion to be described below, is preferably formed from polypropylene.

The inlet 96 includes a bore 107 adjacent the interior of the transducer body 102 and a counterbore 107a having an inside diameter 108 for accepting the nozzle of the canister.

The inside diameter of the bore 107 and the length of bore 107 are dimensioned such that the fluid ejected from the nozzle of the canister is optimized for adequate fluid expansion and flow to the interior of the transducer body. The inside diameter of bore 107 is preferably 0.075 inch, and the length is preferably 0.0825 inch. The inside diameter 108 is dimensioned for the appropriate size of the nozzle 26.

The inlet terminates in an aperture 109 opening into the interior of the transducer body 102. The transducer body is formed in part by the rear inside surface 109a forming a substantially circular face at the extreme upstream end of the transducer body 102 and by the circumferential surface 110, which surface is oriented equidistant about the horizontal axis 58. Concentric with the circumferential surface 110 and coaxial with the horizontal axis 58 is a bluff body 112 formed substantially from a right circular cylinder whose axis is the horizontal axis 58 and against which the mixture is impacted for creating vortices in the transducer body. The upstream portion of bluff body 112 is formed from, or molded with, the center of the rear inside surface 109a of the transducer body 102. Preferably, the surface of the junction of the two is curved and has a radius of curvature. The inside diameter of the circumferential surface 110 is preferably 0.312 inch.

The circumferential surface 110 terminates opposite the rear inside surface 109a in a second circumferential surface 114 for surrounding and holding the lens. The inside diameter of the second circumferential surface 114 is preferably 0.375 inch. The second inside circumferential surface 114 extends from the termination of the circumferential surface 110 to the transducer body rim 106. The distance from the termination of the circumferential surface 110 to the body rim is preferably 0.176 inch.

At the top of the second circumferential surface 114 is molded a substantially hemi-cylindrical woodruff key 116 for orienting and retaining the lens within the transducer body 22. The key preferably has a radius of 0.025 inch and extends substantially the length of the second circumferential surface 114.

The bluff body 112 extends beyond the termination of the circumferential surface 110 almost to a point in a plane defined by rim 106, preferably to within 0.013 inch of the plane of rim 106. The length of the bluff body 112 extends from the rear inside surface 109a a distance of preferably 0.366 inch.

In the bottom surface of the bluff body, on the surface opposite the woodruff key 116, a groove 118 is provided for forming an orifice for creating supersonic vortex flow from the transducer assembly. The groove preferably extends 0.040 inch to the end of the bluff body and has a radius of curvature of 0.012 inch.

A cylindrical lens portion 120 is seated in the volume defined by the second circumferential surface 114 and mounted on the portion of bluff body 112 surrounded by the second circumferential surface 114. The cylindrical lens portion 120 is for focusing and condensing vortically flowing fluid developed by the bluff body 112.

The lens has an outside circumferential face 122 dimensioned to correspond in part with the second circumferential surface 114 of the transducer body 102. The face 122 is dimensioned to form a tapered surface at the upstream end thereof to facilitate an easy but tight, snap-in fit with the transducer body. Additionally, the cylindrical lens portion 120 is provided with a groove 124 in its outside circumferential face corresponding to the woodruff key 116 of the transducer body 102. The diameter of the groove is preferably 0.056 inch. The outside circumferential face 122 is preferably dimensioned such that when placed within the second circumferential surface 114, the cylindrical lens portion 120 is retained by the tight fit of the transducer body 102 and the lens portion 120. If desired, an airtight fit may be provided by ultrasonic or sonic welding.

The cylindrical lens portion 120 is provided with an aperture 126 having an inside diameter corresponding to the outside diameter of the bluff body 112. In order to form a good fit between the lens portion and the transducer body, the outside diameter of the bluff body 112 is preferably 0.072 inch, and the inside diameter of the lens aperture is 0.072 inch. Aperture 126 is formed symmetrically about horizontal axis 58.

A first conically shaped depression 128 is formed in the upstream surface of cylindrical lens portion 120, converging inward toward the aperture 126 and serves to focus the vortices. The maximum diameter of the depression 128 at the upstream edge 130 is preferably 0.322 inch and substantially equivalent to the inside diameter of the circumferential surface 110. The surface of the cone forms an angle of about 57° with the horizontal axis 58. The depression terminates at the aperture 126 having a diameter of 0.072 inch. The height of the conical depression from the upstream edge 130 to the upstream edge of aperture 126 is preferably 0.081 inch.

A second conically-shaped depression 132 extends from the downstream edge of aperture 126 along horizontal axis 58 to the downstream edge 134 of the lens portion 120. The second depression 132 diverges such that the conical surface preferably forms a 45° angle with the horizontal axis 58 for enhancing formation of a large vortex having supersonic flow and a subatmospheric pressure region. The maximum diameter of the depression is preferably 0.133 inch. The aperture 126 preferably extends 0.084 inch along the cylindrical lens portion 120 such that there is a cylindrical volume 136 beyond bluff body 112 before the second conically depression 132 begins for forming the vortices. Preferably, the length of the cylindrical volume is 0.004 inch. The inside diameter is the same as that of the aperture 126.

A second cylindrical aperture 138 is formed in the cylindrical lens portion 120 having an axis 140 extending horizontally and parallel to horizontal axis 58 and is radially offset from aperture 126. The second aperture is provided for concentrating vortices developed at bluff body 112, and the conically-shaped depression 128, and for transporting the flow to the orifice formed by groove 118. The second cylindrical aperture 138 is preferably formed on the side of the bluff body opposite the inlet 96 and on the same side as groove 118. Furthermore, the aperture 138 is formed in the lens portion 120 180° from the woodruff key groove 124. The axis 140 is positioned 0.122 inch from the horizontal axis 58. As a result, the upstream rim of the second aperture is positioned entirely along the surface of the first conically-shaped depression 128.

A third cylindrical aperture 142 is formed in the lens portion 120 extending from the outside circumferential face 122 of the lens portion 120 radially inward to the aperture 126. The third cylindrical aperture 142 is oriented about a second vertical axis 144 which preferably intersects and is at right angles with the horizontal axis 58. Additionally, the horizontal axis 140 preferably intersects and is perpendicular to the second vertical axis 144. The third cylindrical aperture enhances the vortical flow of the mixture due to its 90° configuration with respect to the second aperture 138 and further focuses the flow of the mixture and transports it to the orifice. The second vertical axis 144 is preferably 0.122 inch from the upstream edge 130 of the lens portion 120. The diameter of the third cylindrical aperture 142 is preferably 0.060 inch. As a result, only a portion of the third cylindrical aperture 142 opens into a portion of the groove 118. The remainder of groove 118, specifically between 0.0065 and 0.0125 inch of groove 118, is enclosed within the aperture 126. A nozzle or orifice is thereby formed in the final portion of groove 118 as a result of the intersection of the grooved cylinder with the circular aperture. Due to the circular nature of the third cylindrical aperture 142 as it intersects groove 118, the bottom surface 146 formed by the intersection of the groove 118 and the third cylindrical aperture 142 appears as indicated in FIGS. 2 and 3. Furthermore, the vertical sectional view of the orifice formed by the intersection of the groove 118 with the lens portion 120 is as shown in FIG. 3 comprising two arcs having different radii of curvature. Tests have been conducted wherein the radius of the groove 118 is varied between 0.010 and 0.014 inch, and it has been determined that with the other dimensions described, the optimum radius is 0.012.

The nozzle formed by the intersection of the groove 118 and the third cylindrical aperture 142 is for focusing the fluid obtained from the second cylindrical aperture 138 and third cylindrical aperture 142 for ejection into the cylindrical volume 136 and expansion into the second conically-shaped depression 132. The nozzle forms a single, large vortex having supersonic flow and a subatmospheric region. As described below, the nozzle produces the vortex and assists in centralizing the vortex.

The downstream edge 134 is at the extreme downstream portion of the lens 120. The remainder of the downstream portion of lens 120 extends outwardly and rearwardly, preferably at a 10° angle from the plane defined by the downstream edge 134, to the outside circumferential face 122 of lens 120. The outside face 122 then extends rearwardly to the forward circumferential rim 106 of transducer body 102. The horizontal distance from the downstream edge 134 to the outside circumferential face 122 is preferably 0.021 inch.

As would be apparent, the output of the transducer assembly can be varied by varying the diameters of the various apertures and of the groove. Furthermore, additional apertures may be provided for providing a flow path to the groove 118. However, for flow regimes developed with currently marketed canisters, the configuration of FIG. 1 is preferred.

FIG. 6 shows a schematic of an alternative embodiment of the inhaler 20, including a second resonant screen 148 for performing substantially the same function of the first resonant screen 80 in substantially the same way. Resonant screens 80 and 148 may be used together or alone to achieve the desired flow characteristics.

The operation of the device will now be described with respect to the Figures. The inhaler 20 is assembled as would be apparent to one skilled in the art. The patient then places a container 24 having a mixture of propellant, active medication, and solvent in an inverted fashion into the first body portion 38. The outlet port of nozzle 26 then is confluent with aperture 92 (FIG. 3).

The staging chamber of container 24 is filled with the appropriately metered dose of the mixer of propellant and the medication. The patient then depresses the container relative to the first body portion 38 so that the nozzle 26 is forced further into the mouth of container 24. The interior port to container 24 is thereby sealed and the mixture contained in the staging chamber is ejected under a pressure of between 30 and 50 pounds per square inch, depending upon the particular container being used. The volume of the staging chamber may be approximately 0.05 cubic centimeters so that the total volume of the mixture of propellant and medication is approximately 0.05 cubic centimeters.

As discussed in the '877 patent, the phenomenon of "cold boiling" and/or the resultant atomization of the liquid in the propellant-solvent mixture may occur when the injected mixture is pressurized and then released into the inlet 96. Preferably, the ratio of the gas pressure to the ambient pressure is greater than the critical pressure ratio. For example, the pressure of the mixture in the canister 24 may be approximately 50 pounds per square inch, gage (psig). The propellant to liquid ratio may be typically 30:1 and the volume of output per shot may be 0.05 cubic centimeters.

As a result of the high propellant and liquid pressure, the flow of gas is supersonic as it enters the inlet 96. The ejected fluid then expands into the inlet 96. The fluid flows along the inlet 96 without further significant change in volume or velocity until reaching the transducer body 102, where the mixture again goes through expansion into the chamber defined by the rear inside surface 109*a*, the circumferential surface 110 and the cylindrical lens portion 120. The presence of bluff body 112 in front of the supersonic gas gives rise to a standing shock wave indicated at 150 in FIGS. 2 and 7 and generation of a very large number of vortices indicated at 152. The potential energy, i.e., static pressure, of the gas supplied to the inlet is, in effect, partly converted to kinetic energy—first as an increase in linear gas velocity, then as shock waves, and finally as vortices in the flow passage. The vortices are formed having axes generally parallel to the bluff body 112. The vortices formed at the periphery of the bluff body rotate en masse about axis 58. It is estimated that the pressure at the bluff body 112 in the transducer body 102 is approximately 20–30 psig. The tiny vortices are formed at a rate of approximately 40,000–50,000 vortices per second. This is due to the high velocity of the flow and to the dimensional compactness of the invention, a deliberate and important design criteria. Formation of a maximum number of vortices per unit time is preferred. The number of vortices generated by the device is proportional to the gas velocity and the drag area across which the gas flows and the requisite coefficient of drag.

Because of the pressure differential between the inlet 96 and the first downstream portion 32 created by the pressurized flow of fluid into the inlet, there is a pressure gradient toward the second cylindrical aperture 138 in the first conically shaped depression 128. The individual vortices are impinged on the second aperture in the lens, causing compression thereof into a compressed flow of vortices along the axis 142. The spinning vortices are then forced by the pressure gradient into the third aperture 142 at right angles to the second aperture and forced to flow to the nozzle or orifice. The compacted vortices flow along the second axis 144, impinge on the surface of groove 118, and change direction again to flow at right angles to the second vertical axis and along bottom surface 146. The vortices are thereby further compressed and forced to flow through the cylindrical volume represented at 136 and out to the second conically shaped depression 132. By this process, the vortices are squeezed or compressed into the orifice with sudden expansion into the single large vortex, represented at 154 in FIG. 2, through the second conically shaped depression. The right angle turns through the cylindrical apertures are believed to enhance the vortex effect in the fluid flow.

The cylindrical apertures perform three functions. First, they compensate for changes in operating conditions such as pressure and flow rate, thereby making adjustments unnecessary in many cases. Second, they enhance the vortex action in the device and thus its atomizing power. Third, the cylindrical apertures contribute to the formation of the aerosol from the outlet of the orifice for creating the exiting vortex. These result in superior atomization and/or higher sonic energy generation.

The vortex activity from the bluff body 112 to the final large vortex 154 produces atomization of the liquid fraction in the liquid-propellant mixture so that the medication contained in the liquid fraction is atomized into a mist substantially containing one to three micron-sized monodispersed droplets for entering the first expansion chamber 30. It was found that one massive vortex was formed by impinging the vortices on a rod and letting them escape through an annular chamber. It is believed that once the large number of tiny vortices are created from the bluff body, the vortices can then be manipulated as desired to produce a given result such as the single, large vortex 154.

The single large exiting vortex 154 is comprised of fluid flowing at supersonic velocity due to the compression of the vortices flowing through the orifice and due to the pressure difference across the orifice being greater than the critical pressure. The dose mixture went through a first supersonic flow regime, followed by expansion and creation of vortices. The vortices were then forced through the second and third apertures followed by a second supersonic flow regime out of the orifice and expansion into one large vortex. The pressure on the downstream side of the orifice is approximately atmospheric. The exiting vortex represents a conversion of a substantial amount of static energy to dynamic energy. The vortex is spinning about an approximate center along axis 58 even though the orifice is offcenter. The semicircular, axially extending, wedge-shaped orifice, as seen in transverse cross section, contributes to the centralizing effect on the single vortex. Other configurations for an outlet orifice are contemplated, but the arcuately sectioned circle shown in FIG. 3 is preferred.

The design of the cylindrical lens portion 120 serves several functions. One is to focus the vortex-containing fluid at the orifice. The single cylindrical apertures 138 and 142 provide means for impinging the tightly configured vortices developed about bluff body 112 into focused flow and for increasing the pressure in the flow channels of which the cylindrical apertures are comprised. Because the flow rate in terms of mass times velocity is so low for each dose from the canister, the flow passages must be small enough to maintain the pressure gradient to the first expansion chamber 30 and to provide forward flow velocity for the vortices. The orifice comprising groove 118 and bottom surface 146 is also designed to provide these features and to provide vortex action and supersonic flow, rather than merely squirting the fluid. The dimensions of the orifice are preferably such as to create supersonic flow in the fluid at the output for creating the single vortex, for providing good atomization of the liquid portion of the mixture and to provide a shock wave pattern in the single vortex which also serves to enhance the atomization of the liquid.

A second factor which affects the configuration of the exiting vortex is the propellant to liquid ratio. A limited amount of energy is available for atomization to take place. It is important to ration that energy while still obtaining the desired results. A minimum amount of propellant is desired for a given volume of liquid to maintain the supersonic nature of the exiting vortex, the atomization characteristics thereof and the shock wave pattern produced in the vortex during supersonic conditions. If the relative quantity of propellant is significantly reduced, one or more of these features of the exiting vortex would be affected. However, the design of the transducer lens in the single inlet transducer 22 and the relative proportion of propellant may be adjusted as desired to maintain the desired characteristics of the exiting vortex.

A second design consideration is the formation of the orifice by the conjunction of groove 118 and the bottom surface 146 of the cylindrical lens portion 120. There are various methods for formation of such an orifice including formation of a hole in a cylindrical plug using a laser process, and the formation of a hole through various molding techniques. However, the formation of the hole through molding techniques is often inaccurate and often does not provide consistently reliable results. Molding techniques are especially important where low cost, single inlet transducers of the type shown in FIG. 2 are desired. To overcome the problems in molding a transducer having an orifice with the small dimensions as described above, the design illustrated in FIG. 2 was developed.

As there shown, the small orifice is easily formed by the conjunction of a cylindrical rod having a groove formed therein with a circular aperture extending coaxial with the cylindrical rod wherein the diameter of the aperture is equivalent to the diameter of the cylindrical rod except for the groove cut therein. In this form, a small orifice is formed and problems of tolerances between the rod and aperture are eliminated and problems of variation in dimensions of the orifice are minimized.

The single inlet transducer 22 can accommodate higher flow rates and larger variations in the propellant-to-liquid ratio by changing the dimensions of the interior of the transducer and the cylindrical apertures 138 and 142. Likewise, the groove and the conically shaped depressions in the lens portion 120 may be adjusted as required to produce the desired exiting vortex. Furthermore, additional cylindrical apertures may be provided for producing a symmetrical input to the first expansion chamber with appropriate modification to the orifice. A separate orifice may be provided for each radially extending cylindrical aperture. However, it is preferred to have one set of cylindrical apertures on the side of the bluff body 112 opposite the inlet to take full advantage of the multiplicity of tightly wound vortices produced on the downstream side of bluff body 112.

The single vortex includes a negative pressure zone at the center thereof due to the pressure differential across the orifice being greater or equal to the critical pressure ratio. It has been found that there is enhanced atomization with the disclosed configuration and minimization of deposition of moisture on adjacent surfaces and on a target. It is believed that the particles are electrostatically charged and, therefore, inhibit deposition and recombination or condensation to form larger droplets.

The first expansion chamber provides for expansion of the vortex, thereby reducing the velocity and, therefore, mean free path of the individual medication particles and provides an area for confining the atomized vapor. The expansion and slowing of the particles inhibits condensation of the individual particles and deposition of the particles along the chamber wall. The forward velocity of the particles is transferred to increased random motion of the individual particles. Additionally, it is believed that further atomization of the particles may occur to a limited extent.

As the vortex continues to the second expansion chamber, a like process occurs whereby the forward velocity of the individual particles is further decreased and the vapor vortex is further expanded due to the increased cross sectional area of the second expansion chamber. The effect of the increase in cross sectional area on the vortex is the same as that from the expansion in the first expansion chamber. The second expansion chamber assists in storing the vapor in the vortex, slows the vortex in its forward movement and allows creation of greater vorticity when the fluid reaches the resonant screen, to be described more fully below.

The fluid in the vortex is then impacted on the resonant screen 80 with several resulting effects. The screen resonates to set up a standing wave pattern in the expansion chambers to assist in uniformly dispersing particles in the vortex in the second expansion chamber. It also serves as a drag brake to break up the remaining particles in the vortex. This is enhanced by the fact that a force of drag on the fluid flow is more significant than the force due to the forward momentum of the fluid. Therefore, the effects due to the drag force predominate over the effect due to forward flow of the fluid. Additionally, as the vortex impacts the resonant screen, individual spinning vortices are produced in each square of the resonant screen due to the appearance to the fluid of individual bluff bodies oriented perpendicular to each other. There is also evidence of some vibration in the resonant screen. The position of the screen relative to the transducer and to the expansion chambers maximizes resonant effect and standing wave action, and also the production of the desired particle size, even after the fluid slows down in the expansion chambers.

The final result, after impingement of the fluid on the resonant screen is a soft, "warm", low-velocity mist or vapor to be inhaled by a patient. The mist will have minimal if any impact on the air passageways in the patient's mouth and lungs as the vapor is inhaled. The apparent temperature of the aerosol is more acceptable to the patient also. Additionally, the majority of the propellant will have expanded and dissipated leaving the liquid particles of one to three micron size at the downstream end of the screen without requiring any further impingement of the fluid to obtain the desired particle size. It is believed that the quality and quantity of output is due in part to the combined effect of the supersonic and vortical nature of the transducer output flow and to the resonant screen function.

It has been found, using a mass spectrometer, that the vaporous medication output of the inhaler is approximately 98% of the liquid medication input to the transducer.

The results obtained in the single-inlet transducer combined with the expansion chambers and resonant screens are reproducible for any medication delivery canister presently marketed. The same output is still effected. When the inhaler is manufactured in a plastic molding process, the inhaler may be disposable after completion of a medication regimen from one medication canister. The inhaler is easy to reliably manufacture and easily assembled with press fit parts. The inhaler is compact and convenient to hold and carry.

The transducer of the inhaler is inherently self-adjusting and provides the required particle size output, even with moderate changes in inlet characteristics. However, a point is reached where larger flows in the inlet or other fluid changes, such as propellant-to-liquid ratio, result in a decrease in efficiency of the inhaler. At that point, the transducer would be changed to accommodate the different flow characteristics.

There is sufficient air or other gas in the form of nontoxic propellant and vaporized medication to provide a gas mixture for inhalation. Entrainment of air by the transducer is not required to provide an adequate flow rate of medication. However, it is contemplated that an entrainment valve may be placed behind the transducer with appropriate changes in the body of the inhaler to allow entrainment of air by the pressurized fluid.

Figure 10:
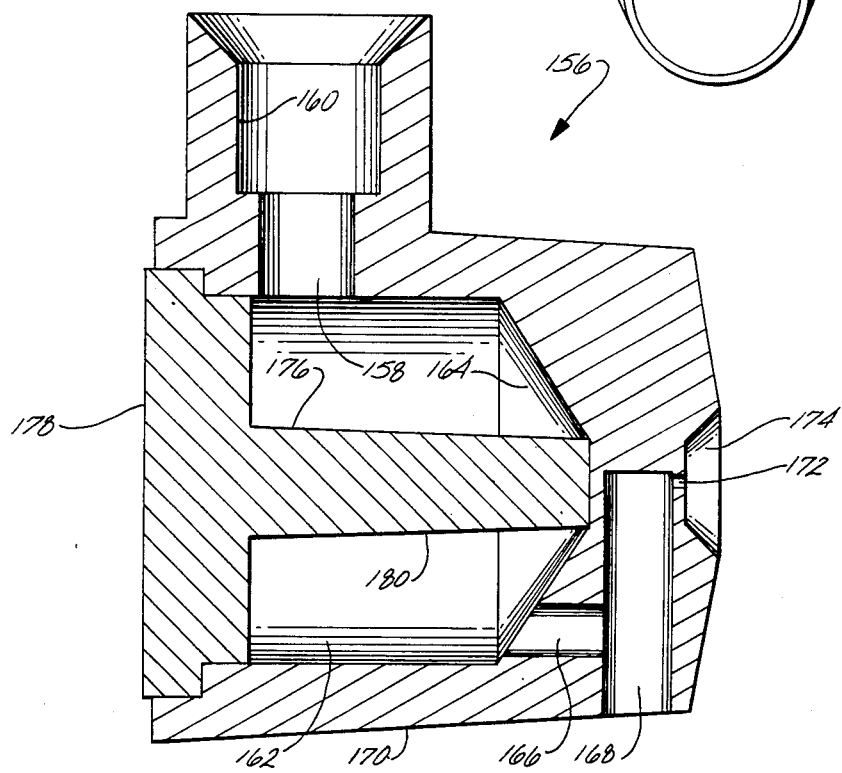
FIG. 10 shows an alternative embodiment of the transducer assembly of FIG. 2.

FIG. 10 shows an alternative embodiment of a transducer in the form of transducer assembly 156. The transducer assembly has a bore 158 in the form of a parallelopiped and a counterbore 160 in the shape of a right circular cylinder. Bore 158 extends to transducer chamber 162 having a converging conical portion 164 formed in the downstream portion thereof. A first cylindrical aperture 166 extends along the first axis (not shown) toward a second cylindrical aperture 168 extending along a second axis (not shown) perpendicular to the first axis. The second axis extends toward a third axis about which the transducer chamber 162 is oriented. The second cylindrical aperture extends from the outside surface 170 of the transducer assembly radially inward slightly past the third axis. A plug (not shown) is provided for sealing the second cylindrical aperture 168 to provide a cylindrical aperture similar to the third cylindrical aperture 142 of FIG. 2. An orifice 172 is formed coaxial with the third axis from the second cylindrical aperture 168 to a diverging conical portion 174. The diverging conical portion is oriented about the third axis. The external dimensions of the transducer assembly 156 are configured in a manner similar to the transducer assembly of FIG. 2 for incorporation into an inhaler.

The transducer assembly includes a tack-shaped bluff body 176 oriented symmetrically about the third axis. The tack-shaped bluff body includes a cap portion 178 for sealing the transducer chamber 162 and a cylindrical portion 180 tapering downward to the converging conical portion in the form of a bluff body 164. The bluff body serves the same function as bluff body 112 described with respect to FIGS. 1 and 2. The bluff body is preferably tapered to assist the flow of the resulting vortices in the direction of the first cylindrical aperture 166.

The transducer assembly 156 is relatively easier to manufacture and mass produce. The operating characteristics of the transducer assembly 156 are similar to those described with respect to the transducer of FIG. 2.

Figure 11:
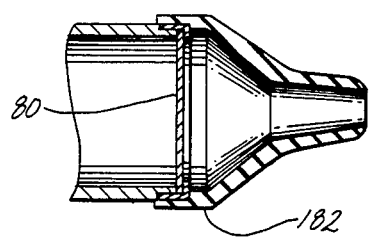
FIGS. 11 and 12 show adapters for the output portions of the inhaler.

FIG. 11 shows a nasal adapter 182 in side section for placement over the resonant screen 80 in the second expansion chamber. This allows nasal intake of the vaporized medication.

Figure 12:
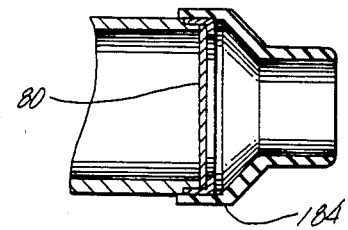

FIG. 12 shows an oral adapter 184 to be positioned over the inhaler 20 in a manner similar to that described with respect to the nasal adapter of FIG. 11. The oral adapter may be beneficial for providing medication to infants and patients who may be incapacitated.

The additional delivery capability as indicated by two important adapters shown in FIGS. 11 and 12 but not limited to these alone, can only be successfully operated if the invention disclosed upstream of these adapters does not produce inertial impaction and does produce droplets which are in the range of one to three microns monodispersed.

It should be noted that the above are preferred configurations but others are foreseeable. The described embodiments of the invention are only considered to be preferred and illustrative of the inventive concept; the scope of the invention is not to be restricted to such embodiments. Various and numerous other arrangements may be devised by one skilled in the art without departing from the spirit and scope of the invention.

What is claimed is:

1. An inhaler for administering a medicine containing aerosol, comprising
    an inlet having a first axis for accepting a discharge tube of a container containing a propellant and a medicant;
    a transducer body having a second central axis along a length of the body and coupled to the inlet wherein the second central axis is normal to a plane containing the first axis and wherein the transducer body comprises an outlet;

a central cylindrical bar coaxial with the second central axis, extending substantially the length of the body and having a free end with a groove formed longitudinally in an outer surface of the bar;

a lens mounted on the free end of the bar to form a substantially airtight fit between the lens and the outer surface of the bar and at least partly within the body;

a first expansion chamber defined by first chamber walls adjacent the body downstream from and adjacent the outlet;

a second expansion chamber defined by second chamber walls downstream from and adjacent the first expansion chamber; and a screen mounted to an end of the second expansion chamber.

* * * * *